(12) United States Patent
Graf et al.

(10) Patent No.: US 9,388,106 B2
(45) Date of Patent: Jul. 12, 2016

(54) SURFACTANT COMPOSITIONS AND USE FOR AQUEOUS COMPOSITIONS

(71) Applicant: Dow Global Technologies LLC, Midland, MI (US)

(72) Inventors: Irina V. Graf, Midland, MI (US); Arkady L. Krasovskiy, Midland, MI (US)

(73) Assignee: Dow Global Technologies LLC, Midland, MI (US)

(*) Notice: Subject to any disclaimer, the term of this patent is extended or adjusted under 35 U.S.C. 154(b) by 234 days.

(21) Appl. No.: 14/027,277

(22) Filed: Sep. 16, 2013

(65) Prior Publication Data

US 2014/0080745 A1    Mar. 20, 2014

Related U.S. Application Data

(60) Provisional application No. 61/701,840, filed on Sep. 17, 2012.

(51) Int. Cl.

| | |
|---|---|
| *B01F 17/28* | (2006.01) |
| *C07C 43/11* | (2006.01) |
| *C09D 7/12* | (2006.01) |
| *B01F 17/00* | (2006.01) |
| *C07C 41/03* | (2006.01) |
| *C09D 5/02* | (2006.01) |
| *C11D 1/72* | (2006.01) |

(52) U.S. Cl.
CPC ............. *C07C 43/11* (2013.01); *B01F 17/0021* (2013.01); *B01F 17/0028* (2013.01); *B01F 17/0092* (2013.01); *C07C 41/03* (2013.01); *C09D 5/027* (2013.01); *C09D 7/1233* (2013.01); *C11D 1/721* (2013.01)

(58) Field of Classification Search
CPC ...... C07C 43/11; C07C 41/03; B01F 17/0021; B01F 17/0028; B01F 17/0092; C09D 5/027; C09D 7/1233; C11D 1/721
USPC .......................................................... 508/579
See application file for complete search history.

(56) References Cited

U.S. PATENT DOCUMENTS

| | | | |
|---|---|---|---|
| 2,932,616 A | 4/1960 | Blake | |
| 4,217,390 A | 8/1980 | Newkirk et al. | |
| 4,241,224 A | 12/1980 | Newkirk et al. | |
| 2003/0153787 A1* | 8/2003 | Carpenter | ............... A61K 8/86 562/592 |
| 2008/0103121 A1* | 5/2008 | Gole | .................... A61K 9/0019 514/202 |

FOREIGN PATENT DOCUMENTS

| | | |
|---|---|---|
| WO | 2008134387 A1 | 11/2008 |
| WO | 2008134389 A1 | 11/2008 |
| WO | 2008134390 A1 | 11/2008 |
| WO | 2009091592 A1 | 7/2009 |
| WO | 2011005246 A1 | 1/2011 |

\* cited by examiner

*Primary Examiner* — Taiwo Oladapo
(74) *Attorney, Agent, or Firm* — Karl E. Stauss; Ronald E. Bakule

(57) ABSTRACT

A surfactant composition selected from the group consisting of: $(R_1O)CH_2$—$CH[(OCH_2CH_2)_{1\text{-}20}OH]$—$CH_2(OR_2)$ and mixtures thereof; wherein at least one of R1 and R2 are secondary alkyl groups including from 3 to 9 Carbon atoms; an aqueous coating composition including an aqueous polymeric dispersion; and certain other compositions including the surfactant composition are provided. Also provided is a method for forming a coating.

5 Claims, No Drawings

SURFACTANT COMPOSITIONS AND USE FOR AQUEOUS COMPOSITIONS

This invention relates to surfactants for aqueous compositions. This invention particularly relates to a surfactant composition selected from the group consisting of; $(R_1O)CH_2$—$CH[(OCH_2CH_2)_{1-20}OH]$—$CH_2(OR_2)$ and mixtures thereof; wherein at least one of R1 and R2 are secondary alkyl groups including from 3 to 9 Carbon atoms. The invention also relates to an aqueous coating composition including an aqueous polymeric dispersion and from 0.1% to 40% by weight, based on the weight of aqueous polymeric dispersion solids, of the surfactant composition, a method for forming a dry coating, and an additional composition.

Surfactants are typically added to compositions such as, for example, emulsion polymers and waterborne paints or coatings that include aqueous dispersions of polymers to function as emulsifiers, pigment dispersants, open time additives, and as freeze/thaw additives. The select $(R_1O)CH_2$—$CH[(OCH_2CH_2)_{1-20}OH]$—$CH_2(OR_2)$ surfactants are, importantly, non-alkylphenol ethoxylates (APEO) and are potentially zero-VOC materials.

Volatile organic compound (VOC) emissions contribute to the creation of ozone, a main constituent of smog. In the US, VOC regulations established by the US Environmental Protection Agency (EPA) and enforced at the state level dictate the maximum concentration of volatile solvents in paints, clean up solvents, and other products. In Europe, VOC limits are defined by the 2004/42/EC Solvents Directive for Decorative Paints. VOC regulations and prohibitions against the use of APEO materials have become more and more stringent and have affected the use of available surfactants.

The present invention serves to provide low or zero VOC compositions including select $(R_1O)CH_2CH(OCH_2CH_2)_{1-20}OHCH_2(OR_2)$ surfactants that are suitable for use in numerous compositions, particularly in compositions that include aqueous polymeric dispersions such as, for example, decorative and protective coatings for various substrates.

International Patent Publication No. 2008/134389 discloses alkylene oxide-extended alkoxylates of linear or branched 1,3-dialkoxy-2-propanol. There continues to be a need for more effective low and no VOC surfactant compositions for uses including in aqueous polymeric dispersions and other compositions that include surfactants. Surprisingly it has been found that surfactant compositions selected from the group consisting of: $(R_1O)CH_2$—$CH[(OCH_2CH_2)_{1-20}OH]$—$CH_2(OR_2)$ and mixtures thereof; wherein at least one of R1 and R2 are secondary alkyl groups including from 3 to 9 Carbon atoms provide superior dynamic surface tension and wetting of polyethylene and Teflon™ while exhibiting very low to moderate foaming properties.

In a first aspect of the present invention there is provided a surfactant composition selected from the group consisting of: $(R_1O)CH_2$—$CH[(OCH_2CH_2)_{1-20}OH]$—$CH_2(OR_2)$ and mixtures thereof; wherein at least one of R1 and R2 are secondary alkyl groups comprising from 3 to 9 Carbon atoms.

In a second aspect of the present invention there is provided an aqueous coating composition comprising an aqueous polymeric dispersion and from 0.1% to 40% by weight, based on the weight of said polymeric dispersion solids, said surfactant composition of the first aspect of the present invention.

In a third aspect of the present invention there is provided a method for forming a coating comprising (a) forming said aqueous coating composition of the second aspect of the present invention; (b) applying said aqueous coating composition to a substrate; and (c) drying, or allowing to dry, said applied aqueous coating composition.

In a fourth aspect of the present invention there is provided a composition comprising from 0.1% to 40% by weight, based on the weight of said composition, surfactant selected from the group consisting of $(R_1O)CH_2$—$CH[(OCH_2CH_2)_{1-20}OH]$—$CH_2(OR_2)$, and mixtures thereof; wherein at least one of R1 and R2 are secondary alkyl groups comprising from 3 to 9 Carbon atoms; said composition being selected from the group consisting of metal working fluids, agricultural formulations, oil and gas recovery formulations, detergents, and emulsifiers.

The present invention relates to a surfactant composition selected from the group consisting of: $(R_1O)CH_2$—$CH[(OCH_2CH_2)_{1-20}OH]$—$CH_2(OR_2)$, preferably $(R_1O)CH_2$—$CH[(OCH_2CH_2)_{1-10}OH]$—$CH_2(OR_2)$, more preferably $(R_1O)CH_2$—$CH[(OCH_2CH_2)_{1-6}OH]$—$CH_2(OR_2)$ and mixtures thereof; wherein at least one of R1 and R2 are secondary alkyl groups comprising from 3 to 9, preferably from 3 to 6 Carbon atoms. Alternatively, the composition may be described as the ethoxylate of 1,3-dialkyl glycerol wherein at least one of the alkyl groups are secondary alkyl groups having from 3 to 9 carbon atoms. Alternatively, the composition may be described as ethoxylated 1,3-dialkoxy-2-propanol, wherein at least one of the alkoxy groups are secondary alkyloxy groups having from 3 to 9 carbon atoms. Preferred secondary alkyl groups are i-propyl, 2-butyl, 4-methylpentan-2-yl, and 2-ethylhexyl, 2,6-dimethylheptan-4-yl.

When only one of R1 and R2 is a secondary alkyl group the other R may be any linear or branched, but not a secondary alkyl group, $C_1$-$C_{10}$ alkyl-; aromatic-; or grouping including hydroxyl, alkoxy-, and chloro- or fluoro-groups. Preferred are n-butyl, 4-methylpentan-2-yl, and 2-ethylhexyl.

The aqueous coating composition of the present invention includes from 0.1% to 40%, preferably from 0.1% to 30%, and more preferably from 0.5% to 20%, by weight based on the weight of the aqueous polymeric dispersion solids, $(R_1O)CH_2$—$CH[(OCH_2CH_2)_{1-20}OH]$—$CH_2(OR_2)$ and mixtures thereof; wherein at least one of R1 and R2 are secondary alkyl groups including from 3 to 9 Carbon atoms surfactant.

The aqueous coating composition of the present invention includes an aqueous polymeric dispersion and from 0.1% to 40% by weight, based on the weight of aqueous polymeric dispersion solids, of the surfactant of the present invention. Typically, the calculated Tg of the aqueous polymeric dispersion is from −25° C. to 110° C. "Calculated Tg" of the polymers herein are those calculated using the Fox equation (T. G. Fox, *Bull. Am. Physics Soc.*, Volume 1, Issue No. 3, p. 123 (1956)). That is, for example, for calculating the Tg of a copolymer of monomers M1 and M2, $$1/Tg(\text{calc.})=w(M1)/Tg(M1)+w(M2)/Tg(M2),$$

wherein

Tg(calc.) is the glass transition temperature calculated for the copolymer w(M1) is the weight fraction of monomer M1 in the copolymer w(M2) is the weight fraction of monomer M2 in the copolymer Tg(M1) is the glass transition temperature of the homopolymer of M1

Tg(M2) is the glass transition temperature of the homopolymer of M2, all temperatures being in ° K.

The glass transition temperature of homopolymers may be found, for example, in "Polymer Handbook", edited by J. Brandrup and E. H. Immergut, Interscience Publishers.

The aqueous polymeric dispersion may be a dispersion of a polymer, oligomer, or prepolymer in an aqueous medium. In some embodiments the aqueous polymeric dispersion may be reactive before, during, or subsequent to film formation. By "aqueous medium" is meant herein a medium including at least 50%, by weight based on the weight of the medium, water. Typical aqueous polymeric dispersions are aqueous dispersions of epoxies, urethanes, acrylic polyols, polyesters, and hybrids and mixtures of these and other chemistries; and addition-polymerized emulsion polymers. The emulsion polymer typically includes at least one addition copolymerized ethylenically unsaturated monomer such as, for example, styrene or substituted styrenes; vinyl toluene; butadiene; (meth)acrylonitrile; a (meth)acrylic ester monomer such as, for example, methyl (meth)acrylate, ethyl (meth)acrylate, butyl (meth)acrylate, hydroxyethyl (meth)acrylate, hydroxypropyl (meth)acrylate, and ureido-functional (meth) acrylates; vinyl acetate or other vinyl esters; vinyl monomers such as vinyl chloride, vinylidene chloride, and N-vinyl pyrollidone. The use of the term "(meth)" followed by another term such as (meth)acrylate, as used throughout the disclosure, refers to both acrylates and methacrylates.

In certain embodiments the emulsion polymer includes from 0% to 6%, or in the alternative, from 0% to 3 wt % or from 0% to 1%, by weight based on the weight of the polymer, of a copolymerized multi-ethylenically unsaturated monomer. It is important to select the level of multi-ethylenically unsaturated monomer so as to not materially interfere with film formation and integrity. Multi-ethylenically unsaturated monomers include, for example, allyl (meth)acrylate, diallyl phthalate, 1,4-butylene glycol di(meth)acrylate, 1,2-ethylene glycol di(meth)acrylate, 1,6-hexanediol di(meth)acrylate, and divinyl benzene.

The emulsion polymer includes from 0% to 15%, preferably from 0.5% to 5%, of a copolymerized monoethylenically-unsaturated acid monomer, based on the weight of the polymer. Acid monomers include carboxylic acid monomers such as, for example, (meth)acrylic acid, crotonic acid, itaconic acid, fumaric acid, maleic acid, monomethyl itaconate, monomethyl fumarate, monobutyl fumarate, maleic anhydride, 2-acrylamido-2-methylpropane sulfonic acid, vinyl sulfonic acid, styrene sulfonic acid, 1-allyloxy-2-hydroxypropane sulfonic acid, alkyl allyl sulfosuccinic acid, sulfoethyl (meth)acrylate, phosphoalkyl (meth)acrylates such as phosphoethyl (meth)acrylate, phosphopropyl (meth)acrylate, and phosphobutyl (meth)acrylate, phosphoalkyl crotonates, phosphoalkyl maleates, phosphoalkyl fumarates, phosphodialkyl (meth)acrylates, phosphodialkyl crotonates, and allyl phosphate.

The aqueous emulsion polymer is typically formed by an addition polymerization emulsion polymerization process as is well known in the art. Conventional surfactants and blends may be used including, for example, anionic and/or nonionic emulsifiers such as, for example, alkali metal or ammonium alkyl sulfates, alkyl sulfonic acids, fatty acids, and oxyethylated alkyl phenols, and mixtures thereof. Polymerizable surfactants that include at least one ethylenically unsaturated carbon-carbon bond which can undergo free radical addition polymerization may be used. The amount of surfactant used is usually 0.1% to 6% by weight, based on the weight of total monomer. Either thermal or redox initiation processes may be used. Conventional free radical initiators may be used such as, for example, hydrogen peroxide, t-butyl hydroperoxide, t-amyl hydroperoxide, ammonium and/or alkali persulfates, typically at a level of 0.01% to 3.0% by weight, based on the weight of total monomer. Redox systems using the same initiators coupled with a suitable reductant such as, for example, sodium sulfoxylate formaldehyde, sodium hydrosulfite, isoascorbic acid, hydroxylamine sulfate and sodium bisulfite may be used at similar levels, optionally in combination with metal ions such as, for example iron and copper, optionally further including complexing agents for the metal. Chain transfer agents such as mercaptans may be used to lower the molecular weight of the polymer. The monomer mixture may be added neat or as an emulsion in water. The monomer mixture may be added in a single addition or more additions or continuously over the reaction period using a uniform or varying composition. Additional ingredients such as, for example, free radical initiators, oxidants, reducing agents, chain transfer agents, neutralizers, surfactants, and dispersants may be added prior to, during, or subsequent to the monomer addition. Processes yielding polymodal particle size distributions such as those disclosed in U.S. Pat. Nos. 4,384,056 and 4,539,361, for example, may be employed. The emulsion polymer may be formed in a multi-stage emulsion polymerization process as are well known in the art. The emulsion polymer is also contemplated to be formed in two or more stages, the stages differing in molecular weight. Blending two different emulsion polymers is also contemplated.

The average particle diameter of the emulsion polymer particles is typically from 40 nm to 1000 nm, preferably from 40 nm to 350 nm. Particle diameters herein are those measured by dynamic light scattering on a Brookhaven BI-90 Plus particle size analyzer.

The aqueous coating composition of the invention is prepared by techniques which are well known in the coatings art. The $(R_1O)CH_2$—$CH[(OCH_2CH_2)_{1-20}OH]$—$CH_2(OR_2)$ surfactant and mixtures thereof; wherein at least one of R1 and R2 are secondary alkyl groups comprising from 3 to 9 Carbon atoms can be added to the coating composition at single or multiple points during the binder synthesis and formulation process. This includes before emulsion polymerization, during emulsion polymerization, after emulsion polymerization, to the pigment grind, during the coating formulation, or to the fully formulated coating composition.

First, pigment(s), if any, are well dispersed in an aqueous medium under high shear such as is afforded by a COWLES™ mixer or predispersed colorant(s), or mixtures thereof are used. Then the emulsion polymer is added under low shear stirring along with the coalescent composition and other coatings adjuvants as desired. The aqueous coating composition may include, in addition to the aqueous polymeric dispersion and optional pigment(s), conventional coatings adjuvants such as, for example, extenders, emulsifiers, coalescing agents other than the coalescent composition of the present invention, plasticizers, antifreezes, curing agents, buffers, neutralizers, thickeners, rheology modifiers, humectants, wetting agents, biocides, plasticizers, antifoaming agents, UV absorbers, fluorescent brighteners, light or heat stabilizers, biocides, chelating agents, dispersants, colorants, waxes, and water-repellants.

Examples of suitable pigments and extenders include titanium dioxide such as anatase and rutile titanium dioxides; zinc oxide; antimony oxide; iron oxide; magnesium silicate; calcium carbonate; organic and inorganic colored pigments; aluminosilicates; silica; various clays such as kaolin and delaminated clay; and lead oxide. It is also contemplated that the aqueous coating composition may also contain opaque polymer particles, such as, for example, Ropaque™ Opaque Polymers (The Dow Chemical Co.).

The amounts of pigment and extender in the aqueous coating composition vary from a pigment volume concentration (PVC) of 0 to 85 and thereby encompass coatings otherwise described in the art, for example, as clear coatings, stains, flat coatings, satin coatings, semi-gloss coatings, gloss coatings, primers, textured coatings, and the like. The aqueous coating composition herein expressly includes architectural, maintenance, and industrial coatings, caulks, sealants, and adhesives. The pigment volume concentration is calculated by the following formula:

$$PVC(\%) = \frac{\text{volume of pigment}(s), +\text{volume extender}(s) \times 100.}{\text{total dry volume of paint}}$$

The solids content of the aqueous coating composition may be from 10% to 70% by volume. The viscosity of the aqueous coating composition may be from 50 centipoises to 50,000 centipoises, as measured using a Brookfield viscometer; viscosities appropriate for different application methods vary considerably.

In the method for forming a coating of the invention the aqueous coating composition is typically applied to a substrate such as, for example, wood, metal, plastics, marine and civil engineering substrates, cementitious substrates such as, for example, concrete, stucco, and mortar, previously painted or primed surfaces, and weathered surfaces. The aqueous coating composition may be applied to a substrate using conventional coatings application methods such as, for example, brush, roller, caulking applicator, roll coating, gravure roll, curtain coater and spraying methods such as, for example, air-atomized spray, air-assisted spray, airless spray, high volume low pressure spray, and air-assisted airless spray. The aqueous coating composition herein expressly includes compositions commonly known as architectural, maintenance, and industrial coatings, caulks, sealants, and adhesives.

Drying of the aqueous coating composition to provide a coating may be allowed to proceed under ambient conditions such as, for example, at 5° C. to 35° C. or the coating may be dried at elevated temperatures such as, for example, from 35° C. to 150° C.

The invention in some of its embodiments will now be further described by reference to the following examples:

EXAMPLE 1

Formation of Surfactant Precursor

Procedure for the Synthesis of
1,3-diisopropoxypropan-2-ol from
2-(isopropoxymethyl)oxirane

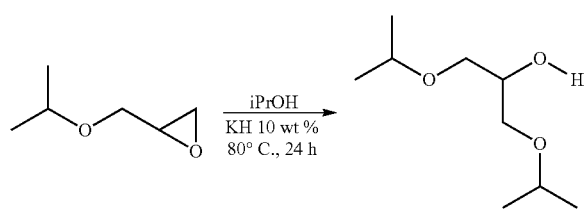

2-(Isopropoxymethyl)oxirane (23.23 g, 25.1 mL, 200 mmol) was dissolved in hexane (20 mL) and placed in reactor. Separately (1.2 g, 20 mmol) of KH was slowly added to (90.1 g, 115 mL, 1.5 Mol) of isopropanol at RT. After deprotonation was complete the solution of potassium isopropoxide in isopropanol was added to the reactor. All operations were performed in a glove box. The reactor was sealed and heated 80° C. for 24 hours. After cooling acetic acid (20 mmols) and ca. 5 g. of powdered talc were added to the reaction mixture followed by filtration through a plug of celite. The solvent was evaporated and the residue distilled under vacuum affording 20.09 g of 1,3-diisopropoxypropan-2-ol.

EXAMPLE 2

Formation of Surfactant Precursor

Procedure for the Synthesis of
1,3-bis((4-methylpentan-2-yl)oxy)propan-2-ol from
epichlorohydrine

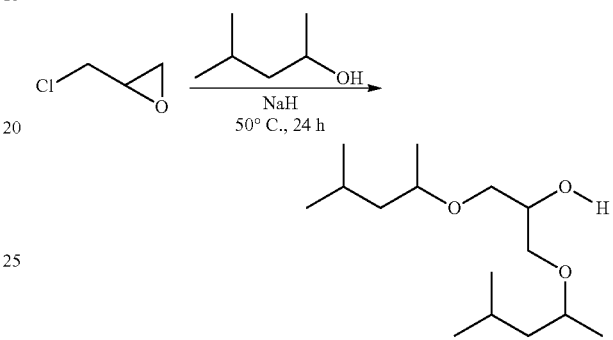

Three necked round bottom flask equipped with a condensor and containing a magnetic stirrer was charged with 100 mL of THF and NaH (2.016 g, 80.00 mmol). Methyl isobutyl carbinol (MIBC, 25.31 mL, 200.00 mmol) was added dropwise to the stirring mixture over 15 minutes at room temperature. The reaction was allowed to stir overnight resulting in a reddish-brown transparent solution. Epichlorohydrine (1.57 mL, 20.00 mmol) was added dropwise. Reaction was kept under heat and stirred for 24 hours. The mixture was allowed to cool to room temperature and AcOH (2.29 mL, 40.00 mmol) was added, followed by 100 mL of hexane. The sample was filtered using a small amount of celite. The solvent was evaporated and the residue distilled under vacuum affording 2.92 g of 1,3-bis((4-methylpentan-2-yl)oxy)propan-2-ol.

EXAMPLE 3

Formation of Surfactant

Procedure for ethoxylation of 1,3-dialkyl glycerol

The dialkyl glycerol (1.00 g), 1,2-dimethoxyethane (1 mL) (the reaction may be conducted without solvent or in any other non-protic solvent), and KH (3-5 mg, 0.3-0.5 wt. %) were loaded into a PPR vial (insert). Alkoxylation was carried out in a Symyx PPR® (Parallel Pressure Reactor) setup containing 48 reactors. Ethylene oxide (EO) was delivered via an Isco syringe pump equipped with a robotically-controlled needle and compressed gas microvalve connected to the PPR, such that required equivalents of EO were added per molecule of amine initiator. A glass insert along with a removable PEEK stir paddle for the cell were dried in a vacuum oven at 125° C. overnight. The insert with the glycerol, 1,2-dimethoxyethane and KH was loaded into each PPR well, heated to 130° C., and pressurized with nitrogen to 50 psi. EO was introduced at 130° C. and the reaction was stirred for 12 h at that temperature. After cooling and venting, the insert was placed in a Savant SC250EXP SpeedVac® Concentrator for 1 h at 80° C. and 0.01 Torr. The resulting viscous surfactants were tested for their properties without additional purification.

EXAMPLE 4

Surfactant Characterization

Selected surfactants, Examples 5-27 and Comparative Examples A-E, synthesized as described in Example 1 or Example 2 followed by ethoxylation as taught in Example 3, were characterized for surfactant properties including dynamic surface tension, substrate wetting (contact angle) and foaming properties. Properties were determined for 0.1 wt % aqueous surfactant solutions at ambient temperature.

Dynamic surface tension was measured using a Hamilton Microstar formulator. During the test, air was dispensed into the vial containing the surfactant solution at a predetermined rate through disposable tips (radius: 0.223 mm), and the instrument recorded pressure changes. From the pressure data collected, bubble rate and maximum pressure values were determined, and dynamic surface tension was then estimated.

The foam test was conducted at ambient temperature using a high-throughput-enabled Phase Characterization and Identification Apparatus (PICA II). Vials were shaken and foam images were collected via a camera. During the test, 1 ml vial containing 0.5 ml of surfactant solution was shaken using the wrist shaker on level #4 for 20 seconds. For each vial, images were collected via a camera: prior to shaking, immediately after shaking. The images were analyzed to determine foam height, expressed in pixels ("px").
Foam heights of 1-200 px are regarded as low foaming. Foam heights of 200-500 px are regarded as moderate foaming.

Contact angle measurements were performed at ambient temperature utilizing a VCA Optima XE (AST Products, Inc.) instrument and corresponding software. The contact angle measurements were performed on a static sessile (i.e. sitting) drop. Five drops of surfactant solution were tested. For each drop, 1 μL of surfactant solution was deposited on the substrate using the syringe in the syringe assembly, an image of the drop on the substrate was recorded immediately after drop placement, and the left and right contact angles were calculated. The final contact angle reported was the average of the left and right contact angles for five drops. Teflon™ and polyethylene surfaces were used as substrates. Teflon™ tape was carefully placed on a glass microscope slide, using a small amount of adhesive on each edge of the microscope slide to hold the Teflon tape on the surface. Clear Filmgard polyethylene films (product #CK410), 4 mil (101.6 um) thick, were cut into 25 mm×75 mm strips, and used as is.

Testing results are summarized in Table 4.1.

TABLE 4.1

Evaluation of selected surfactants-
$(R_1O)CH_2$—$CH(OCH_2CH_2)_nOH]$—$CH_2(OR_2)$

| Example | Structure | DST, 1BR | DST, 10BR | Wetting, Teflon™ | Wetting, PE | Foam Height (px) |
|---|---|---|---|---|---|---|
| 5 | R1 = iPr, R2 = 2-Bu, n = 1 | 35 | 41 | 83 | 48 | 177 |
| 6 | R1 = iPr, R2 = 2-Bu, n = 2 | 35 | 42 | 82 | 54 | 180 |
| 7 | R1 = iPr, R2 = 2-Bu, n = 3 | 33 | 45 | 76 | 52 | 161 |
| 8 | R1 = iPr, R2 = 2-Bu, n = 4 | 31 | 44 | 79 | 51 | 136 |
| 9 | R1 = iPr, R2 = 2EH, n = 1 | 34 | 39 | 82 | 52 | 99 |
| 10 | R1 = iPr, R2 = 2EH, n = 2 | 32 | 38 | 73 | 35 | 102 |
| 11 | R1 = iPr, R2 = 2EH, n = 3 | 31 | 37 | 73 | 53 | 86 |
| 12 | R1 = iPr, R2 = 2EH, n = 4 | 30 | 38 | 71 | 32 | 98 |
| 13 | R1 = iPr, R2 = DIBC, n = 1 | 29 | 37 | 76 | 37 | 33 |
| 14 | R1 = iPr, R2 = DIBC, n = 2 | 29 | 40 | 75 | 46 | 36 |
| 15 | R1 = iPr, R2 = DIBC, n = 3 | 29 | 38 | 70 | 39 | 318 |
| 16 | R1 = iPr, R2 = DIBC, n = 4 | 30 | 42 | 74 | 43 | 293 |
| 17 | R1 = iPr, R2 = MIBC, n = 1 | 32 | 38 | 77 | 49 | 46 |
| 18 | R1 = iPr, R2 = MIBC, n = 2 | 32 | 40 | 80 | 49 | 54 |
| 19 | R1 = iPr, R2 = MIBC, n = 3 | 31 | 43 | 79 | 43 | 136 |
| 20 | R1 = iPr, R2 = MIBC, n = 4 | 30 | 47 | 76 | 56 | 149 |
| 21 | R1 = R2 = MIBC, n = 1 | 32 | 34 | 66 | 52 | 200 |
| 22 | R1 = R2 = MIBC, n = 2 | 30 | 32 | 65 | 42 | 200 |
| 23 | R1 = R2 = MIBC, n = 3 | 30 | 33 | 61 | 42 | 200 |
| 24 | R1 = R2 = MIBC, n = 4 | 29 | 32 | 65 | 34 | 200 |
| 25 | R1 = R2 = MIBC, n = 5 | 30 | 33 | 73 | 50 | 200 |
| 27 | R1 = R2 = MIBC, n = 6 | 30 | 32 | 67 | 35 | 200 |
| Comp. A | R1 = R2 = C7, n = 4 | 42 | 52 | 86 | 70 | 114 |
| Comp. B | R1 = R2 = C7, n = 5 | 42 | 52 | 90 | 66 | 141 |
| Comp. C | R1 = R2 = C7, n = 6 | 46 | 60 | 94 | 77 | 143 |
| Comp. D | R1 = R2 = C7, n = 7 | 42 | 56 | 87 | 72 | 119 |
| Comp. E | R1 = R2 = C7, n = 8 | 50 | 64 | 77 | 63 | 155 |

Note:
2EH = 2-ethylhexyl;
MIBC = alkyl group resulting from methyl i-butyl carbinol, i.e., 4-methylpentan-2-yl;
DIBC = alkylgroup resulting from di i-butyl carbinol;
In Comp. Ex. A-E, C7 is 2-methylheptyl.

Surfactants, Examples 5-27 of the invention, exhibit superior dynamic surface tension and wetting of polyethylene (PE) and TEFLON™, and, in many cases superior foaming properties, relative to the Comparative Examples A-E surfactants.

What is claimed is:
1. A surfactant composition selected from the group consisting of: $(R_1O)CH_2$—$CH[(OCH_2CH_2)_{1-20}OH]$—$CH_2(OR_2)$ and mixtures thereof; wherein at least one of R1 and R2 are secondary alkyl groups comprising from 3 to 9 Carbon atoms.
2. An aqueous coating composition comprising an aqueous polymeric dispersion and from 0.1% to 40% by weight, based on the weight of said polymeric dispersion solids, said surfactant composition of claim 1.

3. The aqueous coating composition of claim 2 wherein said aqueous polymeric dispersion is selected from the group consisting of: aqueous dispersions of epoxies, urethanes, acrylic polyols, polyesters, and hybrids and mixtures of these; and addition polymerized emulsion polymers.

4. A method for forming a coating comprising (a) forming said aqueous coating composition of claim 2;

(b) applying said aqueous coating composition to a substrate; and (c) drying, or allowing to dry, said applied aqueous coating composition.

5. A composition comprising from 0.1% to 40% by weight, based on the weight of said composition, a surfactant selected from the group consisting of: $(R_1O)CH_2\text{—}CH[(OCH_2CH_2)_{1\text{-}20}OH]\text{—}CH_2(OR_2)$ and mixtures thereof; wherein at least one of R1 and R2 are secondary alkyl groups including from 3 to 9 Carbon atoms; said composition being selected from the group consisting of metal working fluids, agricultural formulations, oil and gas recovery formulations, detergents, and emulsifiers.

\* \* \* \* \*